United States Patent [19]

Love et al.

[11] Patent Number: 4,547,590

[45] Date of Patent: Oct. 15, 1985

[54] CARBON MONOXIDE PROCESS FOR THE PRODUCTION OF ALPHA AMINO ACIDS

[75] Inventors: Richard A. Love, Columbia; Lee R. Zehner, Brookeville, both of Md.

[73] Assignee: W. R. Grace & Co., New York, N.Y.

[21] Appl. No.: 628,634

[22] Filed: Jul. 6, 1984

[51] Int. Cl.$^4$ .................................................. C07C 99/00
[52] U.S. Cl. ................................ 562/575; 562/517; 562/406; 562/443; 562/519
[58] Field of Search ............... 562/575, 406, 443, 518, 562/519

[56] References Cited

U.S. PATENT DOCUMENTS

| | | | |
|---|---|---|---|
| 2,413,968 | 1/1947 | Hallowell | 260/534 |
| 3,190,914 | 6/1965 | Williams | 260/534 |
| 3,510,515 | 5/1970 | Colburn, Jr. | 260/534 |
| 3,536,726 | 10/1976 | Fink et al. | 260/295 |
| 3,754,028 | 8/1973 | Lapporte et al. | 260/535 |
| 3,766,266 | 10/1973 | Wakamatsu et al. | 260/534 |
| 3,813,434 | 5/1974 | Marans | 260/534 |
| 3,911,003 | 10/1975 | Suzuki | 260/535 |
| 3,948,977 | 4/1976 | Suzuki | 260/484 |
| 3,948,986 | 4/1976 | Suzuki | 260/535 |
| 4,016,208 | 4/1977 | Suzuki | 260/535 |
| 4,073,804 | 2/1978 | Hearon et al. | 260/534 |
| 4,136,112 | 1/1979 | Bakshi | 562/528 |
| 4,228,305 | 10/1980 | Suzuki | 562/579 |

FOREIGN PATENT DOCUMENTS 2017397  11/1971  Fed. Rep. of Germany ...... 562/575

OTHER PUBLICATIONS

Falbe, Carbon Monoxide in Org. Synth.—123–127, 136–137, 143, 1967.
Souma et al., J. Org. Chem., 38/3633–3635, 1973.
Souma et al., Bull. Chem. Soc. Jap., 46/3237–3240, 1973, (Japan).
Souma et al., Inorg. Chem. 15/968–970, 1976.
Pirozhkov et al., Bull. Acad. Sci. USSR, 25/1264–1267, 1976, (USSR).
Bregeault et al., J. Mol. Cat., 4/225–229, 1978, (Neth.).
Walker, Formaldehyde—220, 515–519, 1964, (U.S.A.).
Kaneko et al., Synth. Prod. and Util. of Am. Acids—114, 1974, (Japan).

*Primary Examiner*—Michael L. Shippen
*Attorney, Agent, or Firm*—Jill H. Krafte

[57] ABSTRACT

A process is disclosed for the synthesis of alpha-amino acid by first contacting the condensation product of an aldehyde or ketone and an amine or amide with a protic or Lewis acid solvent and carbon monoxide to form an intermediate reaction product, and then hydrolyzing the intermediate to yield a product comprising the alpha-amino acid. The reaction rate and product yield can be increased by the addition of a Group 1B metal oxide catalyst in the first step.

9 Claims, No Drawings

CARBON MONOXIDE PROCESS FOR THE PRODUCTION OF ALPHA AMINO ACIDS

BACKGROUND OF THE INVENTION

This reaction relates to the chemical synthesis of alpha-amino acids. More specifically, it relates to the reaction of the condensation product of an amine or amide and a ketone or aldehyde with carbon monoxide ("CO") in the presence of a Lewis acid solvent. The intermediate formed by that reaction is hydrolyzed, under either acidic or basic conditions, to yield an amino acid.

Amino acids, the building blocks of proteins, find wide use in nutritional therapy. Numerous chemical and biological avenues for the synthesis of alpha-amino acids have been explored in efforts to find an efficient and inexpensive means to produce these compounds. For example, U.S. No. 3,190,914 (Williams) and U.S. No. 4,073,804 (Hearon et al.) disclose chemical methods for the preparation of glycine.

Carbon monoxide chemistry has been used in the synthesis of such compounds as hydroxyacetic acid (glycolic acid). For example, U.S. No. 4,016,208 (Suzuki) discloses the preparation of hydroxyacetic acid and oxydiacetic acid by contacting carbon monoxide with formaldehyde and a catalyst consisting essentially of hydrogen fluoride. U.S. No. 3,754,028 (Lapporte et al.) discloses the production of glycolic acid, formic acid and acetic acid by the reaction of formaldehyde, carbon monoxide and water, in the presence of catalytic amounts of a Group VIII noble transition metal compound and an iodide promoter.

Amino acids conventionally are synthesized by the Strecker synthesis, Kaneko et al., *Synthetic Production and Utilization of Amino Acids*, p. 114 (1974). For example, glycine is synthesized by the reaction of hydrogen cyanide, formaldehyde and ammonia to form aminoacetonitrile which then is hydrolyzed to glycine.

SUMMARY OF THE INVENTION

A method of synthesizing alpha-amino acids utilizing carbon monoxide chemistry has been found. The condensation product of an amine or amide and an aldehyde or ketone is further reacted with carbon monoxide using a Lewis acid solvent to form an intermediate reaction product. Hydrolysis of this intermediate yields an alpha-amino acid. The hydrolysis may be conducted under either acidic or basic conditions.

It is an objective of this invention to provide a novel chemical route for synthesizing alpha-amino acids.

Moreover, it is an object to utilize low cost carbon monoxide as one of the key reagents.

An additional objective is to present a method of alpha-amino acid synthesis in which hydrogen cyanide is replaced with a less costly and less hazardous reagent.

DESCRIPTION OF THE INVENTION

The process described herein comprises a two-step method for the synthesis of alpha-amino acids. In the first step, the condensation product of an aldehyde or ketone and an amine or amide is contacted in a reaction vessel with a Lewis acid solvent and carbon monoxide to form an intermediate reaction product. In the second step, the intermediate is hydrolyzed to yield a product comprising an alpha-amino acid. The hydrolysis may be conducted under either acidic or basic conditions. A metal co-catalyst, specifically a Group 1B metal oxide, may be used to enhance the reaction rate and product yield of the first step of this process. The first step reaction rate and product yield also may be increased by conducting the reaction at elevated temperatures and/or pressures.

The Reactants

The choice of initial reactants, i.e., the amines or amides and aldehydes or ketones, will depend on the desired alpha-amino acid product. It can be seen that numerous combinations can be made in accordance with the synthesis described herein. This description will focus primarily on the preparation of glycine, the simplest of the amino acids, for the purpose of illustrating the inventive process. However, various other amino acids or substituted amino acids can be prepared by selecting different aldehydes, ketones, amines and/or amides.

Aldehydes which are suitable for use with this method are of the form R-CHO, where R is hydrogen or an alkyl or aryl group, or substituted form thereof. That is, R may be H, $CH_3$, $C_2H_5$, $C_6H_5$, etc.

Suitable ketones are of the form

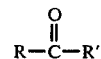

where R and R' are hydrogen or alkyl or aryl groups, or substituted forms thereof. That is, R and R' may be H, $CH_3$, $C_2H_5$, $C_6H_5$, etc.

Suitable amines useful in the method of this invention are of the form $R-NH_2$ where R is hydrogen or an alkyl or aryl group or a substituted form thereof. That is, R may be H, $CH_3$, $C_2H_5$, $C_6H_5$, etc.

Suitable amides useful in the method of this invention are of the form $R-CONH_2$, where R is $NH_2$, hydrogen, or aryl or alkyl groups, or substituted forms thereof. That is R and R' may be H, $CH_3$, $C_2H_5$, $C_6H_5$, etc.

The coupled selection of the desired amine or amide with the desired aldehyde or ketone will depend on which alpha-amino acid is the desired product. The condensation product or products of the amine or amide and aldehyde or ketone may be quite complex. As a result, it may be desirable to select relatively simple starting compounds in order to maintain desired reaction rates, selectivity and yields.

Returning to the embodiment of this process in which glycine is prepared, there are alternative starting compounds which would be suitable. Formaldehyde (HCHO) may be selected as the aldehyde and ammonia ($NH_3$) as the amine. Alternately, formaldehyde may be selected as the aldehyde, with urea ($CO(NH_2)_2$) as the amide.

The selected aldehyde or ketone is reacted with the selected amine or amide to form the condensation product which is used as the amino acid precursor in this process. Conventional reaction techniques are employed, such as those described in Walker, *Formaldehyde*, p. 220 (formation of dimethylolurea) and p. 515-19 (formation of hexamethylenetetramine) (1964). That is, the aldehyde or ketone and the amine or amide are brought into contact with each other and allowed to react. For example, hexamethylenetetramine is formed by reaction of formaldehyde and ammonia gas, which is rapid under ambient conditions and which proceeds quantitatively to completion. Dimethylolurea is produced quantitatively from reaction of neutral or alkaline formaldehyde and urea.

The condensation product of the aldehyde described above with ammonia, and the alpha amino acid produced using these reactants, will have the structures:

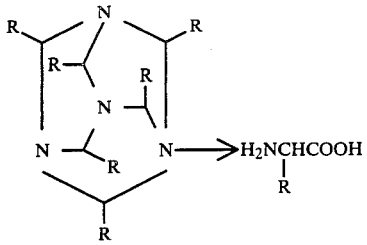

where R is H if the aldehyde is formaldehyde, or an aryl or alkyl group if a higher aldehyde is selected, or substituted forms thereof. The condensation product of these aldehydes with more complex amines, and the alpha amino acid produced using these reactants, will have the structures:

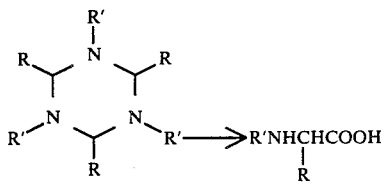

where R is H if the aldehyde is formaldehyde, or an aryl or alkyl group if a higher aldehyde is selected, or substituted forms thereof, and R' is the aryl or alkyl component of the amine selected.

The condensation product of the aldehydes described above with the amides described above will have the structure:

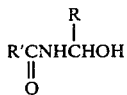

where R is H if the aldehyde is formaldehyde, or an aryl or alkyl group if a higher aldehyde is selected, or substituted forms thereof, nd R' is H if the amide is formamide, NHCRHOH if the amide is urea, or n aryl or alkyl group if a higher amide is selected.

The condensation product of the ketones described above with the amines described above will have the structure:

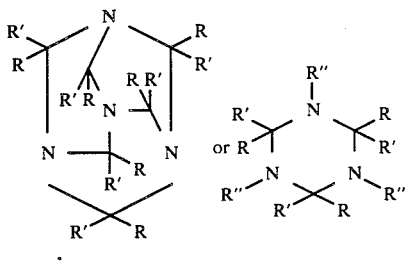

where R, R' and R" may be the same or different and may be H or an aryl or alkyl group or substituted forms thereof.

The condensation product of the ketones described above with the amides described above will have the structure:

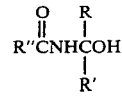

where R, R', and R" may be the same or different and may be H or an aryl or alkyl group or substituted forms thereof.

A number of Lewis acid solvents may be used in the first step of the process of this invention. There are three factors which should be considered in selecting a suitable acid. First, the acid must be strong enough to cause the reaction. That is, it must be capable of forming the carbonium ion to which the CO attaches. Acids with a $pK_a$ value of up to about 4.0 will be most suitable. Second, the acid must have sufficient ability to solvate the carbonium ion so that it will be available to react with the CO. Third, means should be available to readily remove the acid from the amino acid end product after the reaction is terminated. This is conveniently accomplished with acids which are volatile at ambient or elevated temperatures, the upper limit on temperature elevation being that at which decomposition of the amino acid occurs.

Anhydrous hydrogen fluoride ("AHF") is particularly well suited for use as the protic acid solvent in this reaction. Used in the anhydrous form, it will not be corrosive to stainless steel. AHF is a liquid under ambient conditions but is volatile and easily separated from the reaction products by distillation. AHF is a strong acid with a $pK_a$ of 3.45.

Inorganic acids such as sulfuric acid or phosphoric acid can be used, but it may be difficult to separate or remove acids of this type from the amino acid end product. Other acid solvents which may be used for this step include hydrochloric acid, hydriodic acid, and boron trifluride. It is preferred to use anhydrous acids since the water molecules present in aqueous forms will compete with the CO molecules for the binding sites of the carbonium ions.

The CO itself should be free of water for the same reasons. The purity of the CO used is not otherwise critical and lower purity grades will generally be acceptable. For example, synthesis gas ($H_2$, CO, $N_2$ and $CO_2$) is suitable. The CO stream should not, however, contain impurites which themselves will be reactive with the other reactants or with any of the reaction products.

Amino acid yields can be increased by the addition of Group 1B metal oxide catalysts in the first step of the reaction. Suitable catalysts include copper oxide, silver oxide and gold oxide, although copper oxide is preferred due to its low cost.

The Reaction

The process of this invention involves two steps. In the first step ("the carbon monoxide step"), the condensation product described above is reacted with carbon monoxide in a Lewis acid solvent, optionally in the presence of a metal catalyst, to form an intermediate reaction product. This intermediate may comprise alpha-amino acid. In the second step ("the hydrolysis step"), the intermediate reaction product is hydrolyzed to yield alpha-amino acid.

The following is a description of the preferred embodiment of the carbon monoxide step of this process, using AHF as the acid solvent. Variations may be made within the intended scope of the invention and several of these are described below. It will be apparent that variation in process conditions and requirements will be based, in part, on the selection of particular reactants.

Using AHF in the preferred embodiment, it will be necessary to conduct the reaction in a vessel, such as an autoclave, which will confine the reaction. Stainless steel will be a suitable material for the reaction vessel, provided that care is taken to maintain anhydrous conditions in the vessel as hydrogen fluoride is corrosive to stainless steel unless it is kept anhydrous. However, it may be desired to use a disposable Teflon TM (duPont) or polyurethane liner in the reactor. This will facilitate removal of the intermediate reaction product, which then can be washed from the liner, without compromising the anhydrous condition of the reaction vessel itself. A new liner may be added for each batch.

It is also necessary that the reactor be equipped with means for controlling the internal pressure. It may be desired to conduct the reaction at pressures up to about 5000 psi. In addition, the reactor should be equipped with means for cooling the reactor contents to about −20° C. and for heating the reactor contents to about 150° C. The cooling is to maintain the AHF in a liquid state early in the reaction and to dissipate the heat of neutralization on contacting the acid with the aldehyde/ketoneamine/amide condensation product. Warming the contents results in increased product yields. A typical temperature range for conducting this reaction with AHF as the solvent is about 0° C. to about 50° C.

In other embodiments, the requirements for the reactor will vary. For example, if a nonvolatile acid, such as sulfuric acid, is used the reaction easily can be contained without resort to a sealed or pressurized reactor. Moreover, a glass vessel may be used with sulfuric acid. It will be within the knowledge and skill of the process engineer to select or design a reactor suitable for the reaction described herein and the reactants selected.

The reaction vessel preferably is purged with anhydrous CO prior to introduction of the reactants. This will drive out any air and/or mositure which may compete with Co for reaction sites. This is particularly important where AHF is used as the acid, in order to prevent corrosion. Purging may be accomplished by pressurizing the reactor with CO, then venting the vessel two or three times. The CO then preferably is vented to give about one atmosphere of CO within the reaction vessel in order to facilitate introduction of the reactants. In the preferred embodiment, that is, where AHF is selected as the acid solvent, the condensation product then is placed in the vessel. Alternatively, the condensation product may be placed in the vessel prior to CO purging, or the vessel and condensation product may be subjected to a second CO purging step.

In this embodiment, the contents of the reaction vessel are cooled below room temperature. This may be accomplished by placing the reaction vessel in an ice bath, for which it will be most convenient to cool to about 0° C. or by other convenient means. This cooling serves two purposes. First, where a volatile acid is used, the reactor may be cooled to ensure the acid will be a liquid and therefore perform as a solvent. Second, cooling will help to dissipate the heat of neutralization when the acid contacts the condensation product.

After cooling the reactor contents to the desired temperature, the acid is introduced into the reaction vessel. It may be preferred to presaturate the Lewis acid solvent with CO prior to placing the solvent in the reaction vessel, since CO is a reactant. In this embodiment, where AHF or a similar acid is used, the acid solvent is added rapidly to the reactor contents. This rapid introduction of the cool liquid solvent aids in dissipating the heat formed by interaction of the solvent with the substrate. In this manner, charring of the substrate can be avoided. The reactor contents should be stirred or agitated in a manner sufficient to mix the reactants.

In alternative embodiments, that is, when the acid solvent is sulfuric or a similar acid, the preferred procedure will be somewhat different. The acid solvent is saturated with CO and placed in the reaction vessel. The condensation product (substrate) is then added slowly to the reactor under CO in order to enhance the dissolution of the substrate in the acid solvent and to avoid charring of the substrate. The reactor contents should be stirred or agitated in a manner sufficient to mix the reactants.

The vessel then preferably is pressurized with CO. This increased pressure serves to drive the reaction by increasing the concentration of CO in solution. The pressure range can be up to about 5000 psi, with up to about 1500 psi preferred. In addition, there is a rapid pressure drop of up to about 100 psi following pressurization with CO as long as CO is being absorbed, that is, as long as the reaction is still occurring. This can be used to detect reaction completion. An appropriate time for termination of the reaction can be determined by continuing to re-pressurize the reaction vessel and observe whether the pressure drops. When little or no pressure drop is observed, the reaction may be terminated.

Concurrently, the temperature of the vessel and its contents may be raised to increase the reaction rate and yield. The temperature may be raised to about 100° C. by placing the vessel in a heater bath or by any convenient means. There is a slow rise in pressure as the reactor contents are warmed. However, the rapid pressure drop described above still may be observed following pressurizing with additional CO.

When the reaction is terminated, the excess gases in the vessel are vented through a scrubber or other facility. If it is desired to recycle CO, the reactor may be cooled prior to this step so that all or substantially all the remaining AHF is in the liquid phase prior to venting of the CO from the reactor. Scrubbed CO may be recycled for further use in the CO step of this method, although care should be taken to keep it free from moisture or to return it to an anhydrous condition before re-use.

Following venting of the CO, it may be desired to purge the vessel of volatile acid solvent with argon or some other gas inert to the reactants and to the intermediate reaction product. If the vessel has been cooled for removal of CO, its contents should be warmed to about room temperature or somewhat higher prior to purging in order to volatilize any AHF remaining in the reaction system. However, temperatures above about 30° C. may cause charring of the reactor contents. The purging gas should be anydrous, particularly if AHF is used as the acid. Purged volatile acid is conducted to a scrubber or the like. Recycle of the volatile acid solvent may be desired.

The reactor contents at this point comprise the intermediate reaction product, which is an amber, clear, glasslike substance. Infrared analysis of this intermediate indicates a strong amide band. At least a portion of the intermediate produced may be the desired alpha-amino acid (see Example III). The intermediate may be washed from the reaction vessel or liner with water. Alternatively, the hydrolysis step may be conducted in the reactor as long as it is thoroughly dried before re-use.

The second step of the process of this invention comprises hydrolysis of the intermediate reaction product to form a product comprising an alpha-amino acid. This step may be conducted using conventional hydrolysis techniques and may be conducted under acidic or basic conditions with any aqueous protic 3 to 4N acid or base. If basic hydrolysis conditions will be employed, it may be necessary or desirable to neutralize any remaining protic acid solvent before hydrolyzing. Most common inorganic bases, sodium hydroxide, for example, will be suitable. For the hydrolysis, about two to about four, preferably about three, equivalents of acid or base are added in relation to the amount of condensation product used in the CO step. After adding the acid or base for the hydrolysis, the temperature is elevated to about 80° to 120° C., preferably about 100° C., for about 1 to about 24 hours, preferably about 5 to about 8 hours, with sufficient stirring or other mixing to agitate the system.

HPLC analysis of the hydrolyzed product demonstrates that alpha-amino acid is a component of the product. The alpha-amino acid component may be separated and recovered by conventional purification techniques.

In an alternative embodiment of this method, a metal catalyst may be used to increase the reaction rate and yield in the carbon monoxide step. Any of the metal catalysts described above can be added to the first step reaction mixture. Alternatively, two or more of these metal catalysts may be combined for use in this step. The ratio of 1B metal catalyst to condensation product can range from about 1:20 to about 2:1. The metal catalyst should be well-dispersed in the reaction solution by stirring or other mixing.

The Examples which follow are given for illustrative purposes only and are not meant to limit the invention described herein. The following abbreviations have been used throughout in describing the invention:

AHF—anhydrous hydrogen fluoride
atm—atmosphere(s)
CO—carbon monoxide
°C—degrees Centigrade
HPLC—high pressure liquid chromatography
ml—milliliter(s)
%—percent
psi—pounds per square inch

EXAMPLE I

Hexamethylenetetramine (2.03 gm, $1.45 \times 10^{-2}$ moles) (Aldrich Chemical Company), the condensation product of ammonia and foramldehyde, was placed in a 120 ml polyethylene-lined autoclave, which was sealed and purged by pressurizing to 50 psi with CO and venting. Purging nd venting was repeated three times. The autoclave was cooled to 0° C. with an ice bath. Anhydrous hydrogen fluoride (3:0 ml) was injected all at once into the autoclave.

The ice bath was removed and replaced with a heater bath to heat the autoclave contents to 50° C. Between 0° C. and 20° C., the autoclave was pressurized to 1400 psi with CO. A rapid pressure drop of 100 psi was observed following pressurization. This was followed by a slow rise in pressure as the autoclave warmed to 50° C.

After 3 hours, the autoclave was vented and purged overnight of volatile hydrogen fluoride with an argon stream. The product was washed out of the liner with 30 ml de-ionized water. This crude intermediate product was found, by infrared anaylsis, to contain a strong amide band.

Half of the reaction product was acidified with 1.0 ml 97% $H_2SO_4$ and heated to 100° C. for 23 hours. Anaylsis by HPLC (orthophthalaldehyde derivitization) determined that a major reaction product was glycine (17-20% based on nitrogen equivalence in hexamethylenetetramine).

The AHF remaining in the other half of the reaction product was neutralized with 12 ml 4N KOH. An additional 3.2 gm ($6 \times 10^{-2}$ M) KOH was added for the hydrolysis. The solution was heated to 100° C. for 12 hours. Anaylsis by HPLC (orthophthalaldehyde derivitization) determined that the major product was glycine (51% based on nitrogen equivalence in hexamethylenetetramine).

EXAMPLE II

N,N'Dimethylolurea (0.7469 gm, $6.22 \times 10^{-2}$ moles) (Aldrich Chemical Company), the condensation product of urea and formaldehyde, was placed in an 80 ml Teflon (TM) (duPont) lined stainless steel autoclave. The autoclave was sealed, cooled to 0° C. with an ice bath, and purged three times with 50 psi carbon monoxide. Anhydrous hydrogen fluoride (30 ml) was injected into the autoclave. The compounds were so reactive in absorbing CO that no heater bath was used. The autoclave was pressurized to 80 psi with CO. An immediate rapid pressure drop of 15 psi was observed.

After 6 hours, the system was vented and the contents removed. The reaction contents were neutralized with aqueous calcium hydroxide. The resultant calcium sulfate precipitate was removed by filtration. Sodium hydroxide (0.5 gm, $1.25 \times 10^{-2}$ moles) was added to the filtrate and heated to 100° C. for 8 hours. A white precipitate was removed by filtraton. The remaining clear solution was determined by HPLC (orthophthalaldehyde derivitization) to contain glycine (3.9% based on nitrogen equivalence in dimethylolurea).

EXAMPLE III

Copper oxide (1.5023 gm, $1.05 \times 10^{-3}$ moles) was placed in 50 ml 97% sulfuric acid saturated with carbon monoxide in a 100 ml round bottom flask. When the solution clarified (about 10-20 minutes), hexamethylenetramine (0.8053 gm, $5.74 \times 10^{-3}$ moles) (Aldrich Chemical Company) was added slowly under CO. The system was stirred to mix under 1.0 atm CO at room temperature for 23 hours. The reaction composition was analyzed by HPLC (orthophthalaldehyde derivitization) and was determined to contain glycine as a major product (41% based on nitrogen equivalence in hexamethylenetetramine). The hydrolysis step of the invention was not conducted in this experiment.

EXAMPLE IV

The procedures of Example III were repeated, using the same reactants in the same quantities, except that the copper oxide catalyst was not added. The reaction composition was analyzed by HPLC (orthophthalaldehyde derivitization) and was determined to contain glycine (2.2% based on nitrogen equivalence in hexamethylenetetramine).

The principles, preferred embodiments and modes of operation of the present invention have been described in the foregoing specification. The invention which is intended to be protected herein, however, is not to be construed as limited to the particular forms disclosed, since these are regarded as illustrative rather than restrictive. Variations and changes may be made by those skilled in the art without departing from the spirit of the invention.

What is claimed is:

1. A method for the synthesis of glycine comprising:
   (a) contacting in a reaction vessel:
      (i) the condensation product of formaldehyde and ammonia or urea,
      (ii) a Lewis acid solvent characterized in that it is capable of forming the carbonium ion of said condensation product, is capable of solvating said carbonium ion so that it is available for reaction, and can be readily removed from the alpha-amino acid product after the reaction is terminated, and (iii) carbon monoxide,
   (b) forming an intermidate reaction product, and
   (c) hydrolyzing said intermediate reaction product to yield a product comprising glycine.

2. The method of claim 1 in which said acid solvent is hydrofluoric acid, hydrochloric acid, hydriodic acid, sulfuric acid, phosphoric acid, or boron trifluoride.

3. The method of claim 2 in which said acid solvent is anhydrous hydrofluoric acid.

4. The method of claim 1 in which said condensation product is hexamethylenetetramine, the condensation product of formaldehyde and ammonia.

5. The method of claim 1 in which said condensation product is dimethylolurea, the condensation product of formaldehyde and urea.

6. The method of claim 1 in which one or more Group 1B metal oxide catalysts are present in the reaction vessel in step (a).

7. The method of claim 14 in which said Group 1B catalyst is copper oxide, silver oxide or gold oxide.

8. A method of the synthesis of glycine comprising contacting in a reaction vessel: (i) hexamethylenetetramine, (ii) a Lewis acid solvent characterized in that it is capable of forming the carbonium ion of hexamethylenetetramine, is capable of solvating said carbonium ion so that it is available for reaction, and can be readily removed from the alpha-amino acid product after the reaction is terminated, (iii) carbon monoxide and (iv) one or more Group 1B metal oxide catalysts.

9. The method of claim 8 in which said Lewis acid solvent is sulfuric acid.

* * * * *